United States Patent [19]
Parekh

[11] Patent Number: 5,141,507
[45] Date of Patent: Aug. 25, 1992

[54] SOFT INTRAOCULAR LENS

[75] Inventor: Ramesh V. Parekh, Irvine, Calif.

[73] Assignee: Iolab Corporation, Claremont, Calif.

[21] Appl. No.: 804,145

[22] Filed: Dec. 6, 1991

[51] Int. Cl.⁵ ............................................. A61F 2/16
[52] U.S. Cl. ........................................ 623/6; 623/901; 264/1.7
[58] Field of Search ................ 623/6, 901; 264/1.1, 264/1.7

[56] References Cited

U.S. PATENT DOCUMENTS

| | | |
|---|---|---|
| 4,139,915 | 2/1979 | Richards et al. ................. 623/6 |
| 4,468,820 | 9/1984 | Uhler et al. ..................... 623/6 |
| 4,573,998 | 3/1986 | Mazzocco ....................... 623/6 |
| 4,615,702 | 10/1986 | Koziol et al. .................... 623/6 |
| 4,687,484 | 8/1987 | Kaplan ........................... 623/6 |
| 4,790,846 | 12/1988 | Christ et al. .................... 623/6 |
| 4,834,751 | 5/1989 | Knight et al. ................... 623/6 |

*Primary Examiner*—Ronald Frinks
*Attorney, Agent, or Firm*—Matthew S. Goodwin

[57] ABSTRACT

A soft intraocular lens with an insert which can be molded into an optic having an optic attachment member embedded in the optic and a haptic attachment member extending out of the optic to which a haptic may be connected. The insert permits the easy attachment of the haptic to the optic without subjecting the haptic material to the rigors of the processes by which the soft optic is made.

4 Claims, 2 Drawing Sheets

SOFT INTRAOCULAR LENS

FIELD OF THE INVENTION

The present invention relates to soft intraocular lenses, and more particularly, to means for joining one or more haptics, or filamentary support members, to the optic of an intraocular lens.

BACKGROUND OF THE INVENTION

In the human eye, light enters through the cornea (front surface of the eye) passes through the natural lens of the eye (behind the iris) to the retina. The natural lens of the eye is a clear, gelatinous substance enclosed in a transparent capsular bag, whose periphery is connected to the muscles within the eye by suspensory ligaments called zonules. As one ages, one's lens sometimes becomes cataract, a pathological condition in which the lens progressively clouds, hardens and ultimately opacifies to slowly reduce the amount of light passing through the lens to the retina. Intraocular lenses are implants used to replace the cataract natural lens to restore sight.

There are various well-known intraocular lens designs. An implanted lens may be placed between the cornea and the iris in the anterior chamber or behind the iris in the posterior chamber of the eye. Intraocular lenses generally have two parts. The first part is the optic which is centrally placed within the eye between the cornea and the retina in either the anterior or posterior chamber. The second part of the lens is called a haptic which extends from the optic and supports the optic in its proper position within the eye. With many present lenses, the optics are made of a hard, biocompatible acrylic material like polymethylmethacrylate (PMMA) which has good refractive optical characteristics. The optics are generally circular in cross section and have diameters which vary between 5 mm and 7 mm. The haptics are usually made of a flexible, filamentary material which extend from the periphery of the optic to the surrounding anatomy of the eye to hold the optic in place.

In the past, some haptic supports have been made of metal wire like platinum. They have been attached to PMMA optics by heating the end of the platinum haptic to a temperature higher than the melting temperature of the optic and then inserting the heated end into the plastic of the optic. The plastic melts to permit the metal wire to be inserted and then solidifies around the metal haptic to hold it in place.

Other lenses have used polypropylene haptics which can be attached to PMMA optics by drilling holes in the optic, inserting the end of the polypropylene haptic into the hole and holding it in position by, for example, bonding the polypropylene to the PMMA or crimping the PMMA around the periphery of the polypropylene to mechanically lock it in place.

When one inserts rigid optics into the eye, one must make an incision slightly larger than the diameter of the optic. It is desirable to use the smallest incision possible. In the past, the diameter of the rigid optic has been the limiting factor on the size of the incision in the eye.

In order to reduce the size of the incision one may use an optic made of a soft, flexible material like silicone elastomer, polyurethane elastomer, hydrogel plastics, collagen, organic or synthetic gels or combinations of these materials. Since these materials are soft and flexible the conventional methods of mounting haptics to optics generally do not work as well. For example, one cannot drill holes in soft silicone optics into which the end of the haptics can be fastened by heat staking.

One method of attaching haptics to flexible optics is shown in U.S. Pat. No. 4,615,702 where an annular ring from which integral haptics extend is embedded in the soft material of the optic when the optic is molded.

In U.S. Pat. No. 4,790,846 haptics are separately molded into the soft optic and have various geometric configurations at the point where they are embedded in the optic like bulbous enlargements, loops, barbs, and the like to try to secure the haptic into the optic.

In U.S. Pat. No. 4,834,751 an arcuate anchor is attached to one end of a haptic and molded into a soft optic.

Since the haptics for soft lenses are usually insert-molded into the lens, the material of which the haptic is made must be selected so that it will not be affected or degraded during the molding process. Polypropylene haptics can be insert-molded into silicone optics, but care must be taken not to damage the very small diameter haptic filaments or alter the haptic geometry during the thermal cycles that are required to cure a silicone material. In some instances, it is desirable to make the haptic supports of PMMA. However, PMMA haptics may melt at temperature above the molding temperature of silicone and thus cannot be directly insert-molded into silicone optics.

It would be desirable to have an improved means for mounting conventional haptics made of well-known and accepted haptic materials into the materials from which soft intraocular lens optics are made, without concern for haptic degradation.

SUMMARY OF THE INVENTION

The present invention provides an insert means for attaching a haptic to a flexible, molded optic of a soft intraocular lens. The optic can be molded about the insert means, and the insert means can be made of a variety of materials which will not be damaged during the process of molding the optic. The insert means which allows for attachment of the haptic to the flexible optic includes an optic attachment member having an aperture through it. The optic is molded about the optic attachment member and within the aperture so as to securely fasten the optic attachment member to the flexible optic. The insert means also has a haptic attachment member integral with the optic attachment member. The haptic attachment member has a bore therein for receiving the haptic. This permits any suitable material to be used for the haptic and one need not worry about damaging the delicate haptic filaments during the process of manufacturing the optic.

Typically, two haptics are attached to the optic at diametrically opposed positions. One may use one insert means for each haptic and the insert means are preferably connected to each other only by the material of the optic. It would also be possible to replace separate optical attachment members for each insert means with a single annular optical attachment member which would be embedded inside the periphery of the optic. Separate haptic attachment members for each haptic can be integrally connected to such an annular optic attachment member.

In the preferred embodiment, the optic could be made of silicone and the haptics could be made of polypropylene or PMMA. Other materials could be used for the optic including polyurethane elastomers, hydrogel plastics, collagen, organic or synthetic gels, or combinations of these materials. The insert means could be made of any material which would not be damaged during the process of molding the optic about it, for example polysulphone. Other material could be used, such as engineering thermoplastics, thermoset plastics, ceramic, metal or composite materials.

These and other features of the present invention will be appreciated when one reads the following description of the preferred embodiment of the invention taken together with the following drawings.

DESCRIPTION OF THE PREFERRED EMBODIMENT

Figure 1:
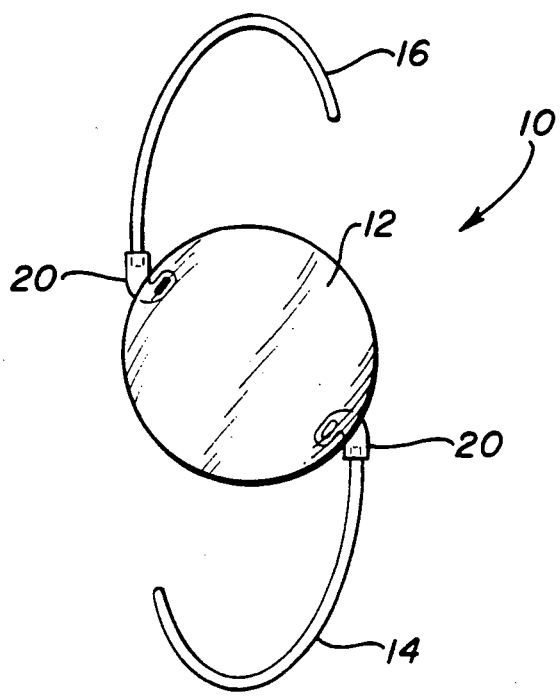
FIG. 1 shows an intraocular lens utilizing the present invention to connect a soft optic with flexible haptics shown in plan view.
Figure 2:
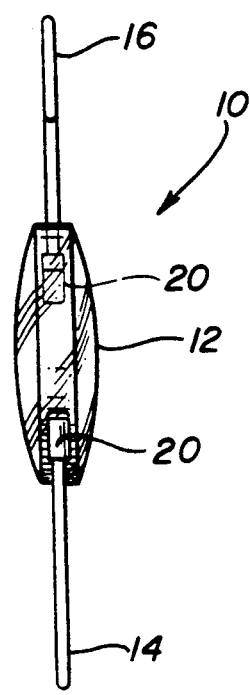
FIG. 2 shows a side view of the lens of FIG. 1.

Referring now to FIG. 1 there is shown a representative intraocular lens 10 with which the present invention can be used. Lens 10 has an optic 12 made preferably of silicone, but alternatively, of any flexible biocompatible material like polyurethane elastomers, hydrogel plastics, collagen, organic or synthetic gels or any combination of these materials. Extending from optic 12 are two filamentary supporting members, or haptics 14 and 16 preferably made of polypropylene or polymethylmethacrylate, but alternatively made of any suitable haptic support material. The configuration of the haptics can be any of the conventional configurations used for the manufacture of intraocular lenses. The configuration of the haptics shown in FIG. 1 is what is conventionally referred to as the modified "J-loop" configuration.

Insert means 20 attach haptics 14 and 16 to optic 12, and can be made of any material which would not be damaged during the manufacturing process for embedding it in the optic. For a silicone optic, a polysulphone insert could be used or other suitable material depending on the material of which the optic is made. The insert means can be made using traditional manufacturing processes. For example, if the insert means is derived from a polymeric material, it can be fabricated from such polymeric material by molding or casting, machining or any other conventional plastic processing.

Figure 3:
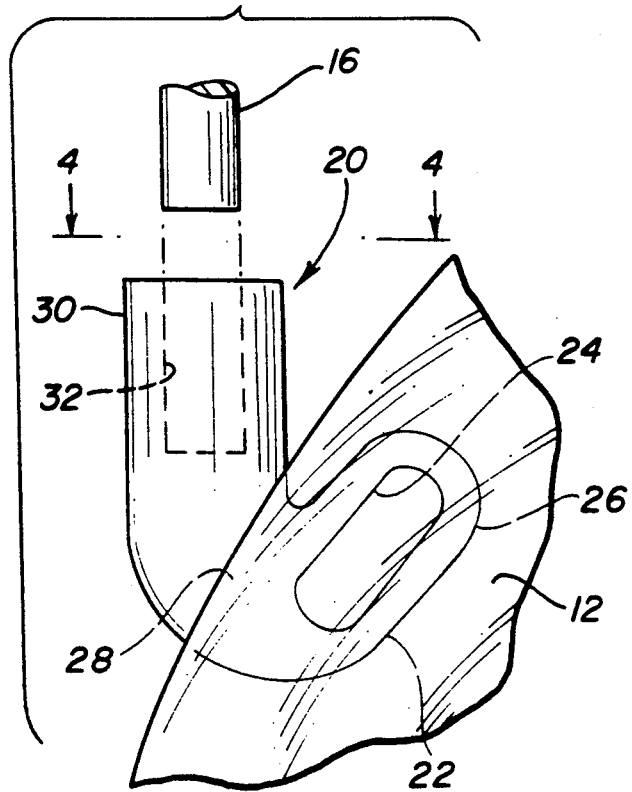
FIG. 3 shows a partial detail plan view of a portion of the lens shown in FIG. 1.
Figure 4:
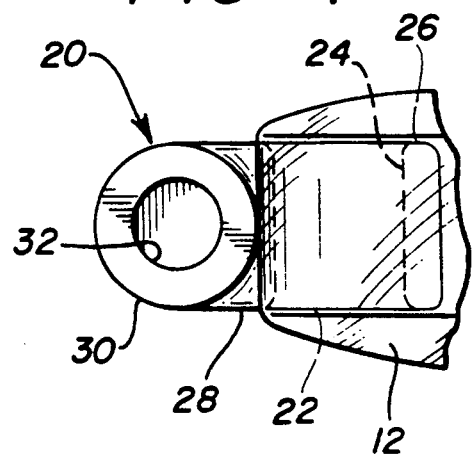
FIG. 4 shows a partial top view of the portion of the lens shown in FIG. 3 taken along lines 4—4 in FIG. 3.
Figure 5:
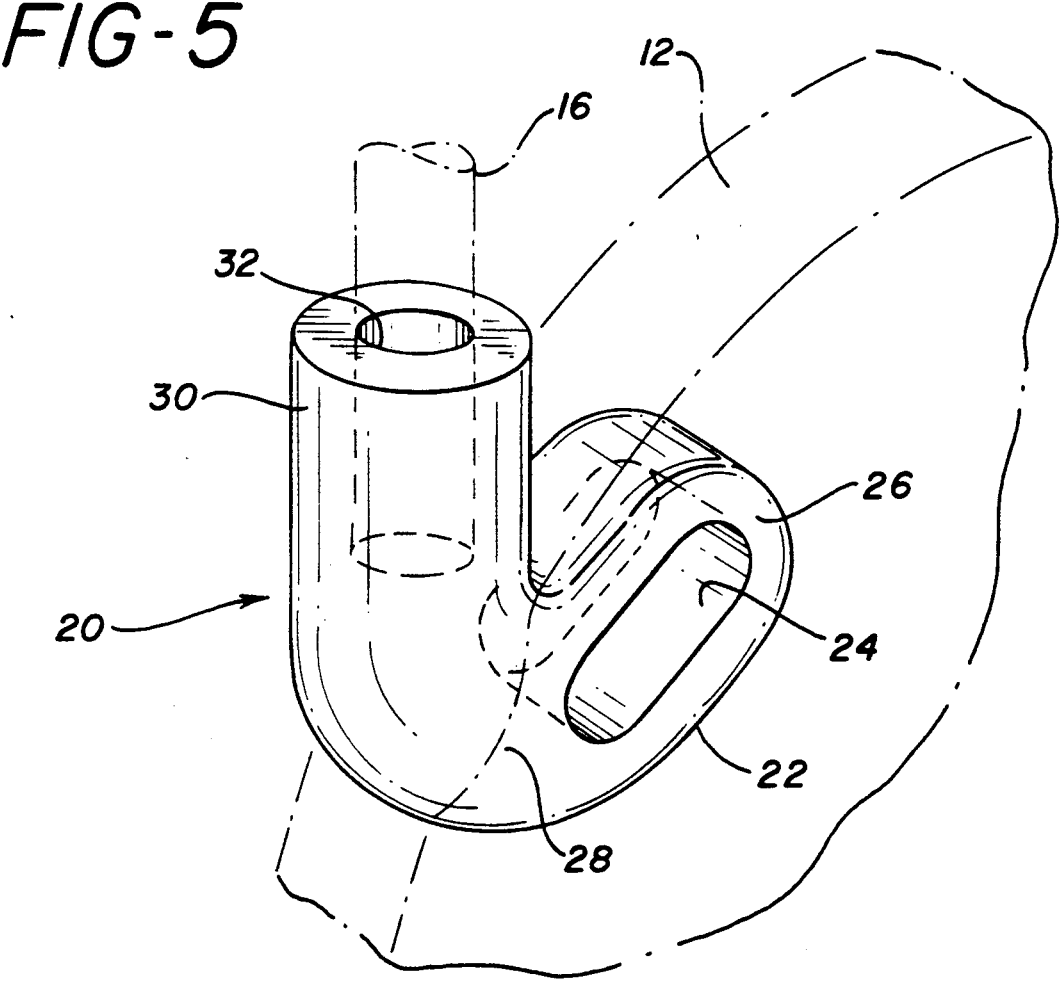
FIG. 5 shows a partial perspective view of the lens of FIG. 1.

Referring now to FIGS. 3 and 4, insert means 20 includes an optic attachment member 22 embedded within optic 12. Member 22 has a relatively large aperture 24 completely through it with a surrounding periphery 26. When the optic 12 is molded about the optic attachment member of the insert means in a suitable mold cavity configuration for the desired shape of the optic, the material of which the optic is made fills aperture 24 to lock optic attachment member 22 into optic 12. Insert means 20 also includes a haptic attachment member 30 integrally bound to optic attachment member 22 at or near the peripheral edge 28 of optic 12. Haptic attachment member 30 includes a bore 32 therein for receiving one end of haptic 16. Haptic 16 may be attached to haptic attachment member 30 by bonding, welding, crimping or any of the well-known methods of attaching haptics to optics.

The insert of the present invention allows one to use any desired method of attaching haptics to the flexible optic by selecting the properties of the material from which insert means 20 is made.

The invention has been described in conjunction with the preferred embodiment. Those skilled in the art will appreciate that many modifications and changes may be made to the preferred embodiment without departing from the scope of the invention. It is, therefore, not intended to limit the present invention except as set forth in the appended claims.

I claim:

1. A soft intraocular lens of the type having a flexible molded optic, a haptic for supporting said optic within the eye, and insert means for attaching said haptic to said flexible optic, the improvement wherein the insert means comprises:

an optic attachment member having an aperture therethrough, said flexible optic molded about said optic attachment member and within said aperture so as to securely fasten said optic attachment member to said optic; and a haptic attachment member integral with said optic attachment member having a bore therein for receiving said haptic.

2. The lens of claim 1 wherein said lens has two haptics, and said insert means are used to attach each haptic to said flexible optic.

3. The lens of claim 1 wherein said haptic is composed of polypropylene.

4. The apparatus of claim wherein said haptic is composed of polymethylmethacrylate.

* * * * *